Figure 1:
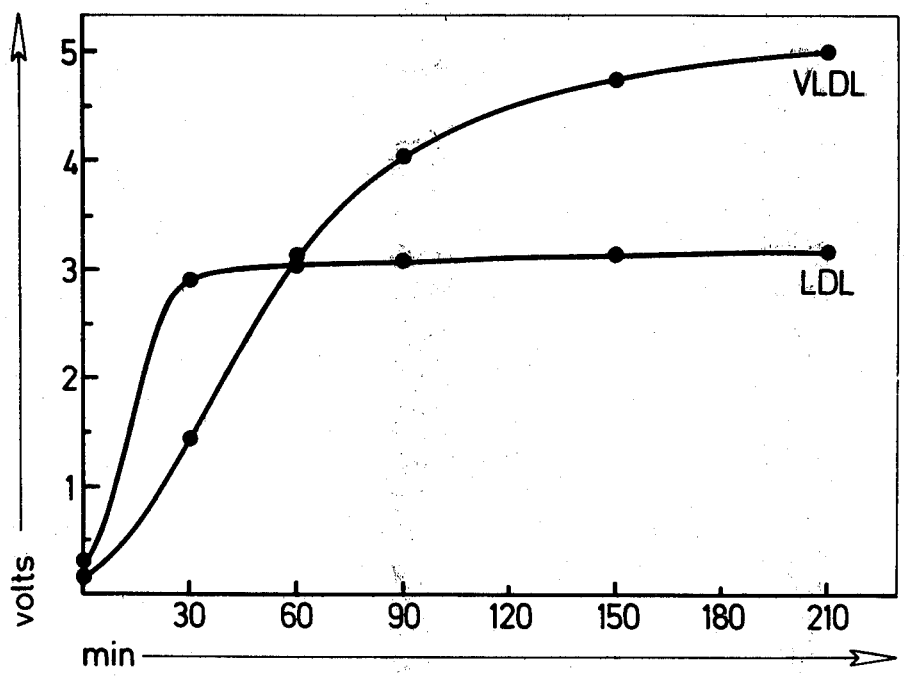

United States Patent [19]

Heuck

[11] 4,311,788
[45] Jan. 19, 1982

[54] PROCESS FOR THE QUANTITATIVE DETERMINATION OF A SERUM PROTEIN IN TURBID SERUM AND PLASMA SAMPLES

[76] Inventor: Claus-Christian Heuck, Hoechst Aktiengesellschaft, D-6230 Frankfur/Main 80, Fed. Rep. of Germany

[21] Appl. No.: 54,486

[22] Filed: Jul. 3, 1979

[30] Foreign Application Priority Data

Jul. 5, 1978 [DE] Fed. Rep. of Germany ....... 2829531

[51] Int. Cl.³ .................... G01N 33/54; G01N 33/68; G01N 21/47
[52] U.S. Cl. .................................... 435/7; 23/230 B; 23/915; 252/174.12; 252/408; 424/12; 435/19
[58] Field of Search ......... 23/230 B; 252/408, 174.12; 424/12; 435/7, 18, 19

[56] References Cited

U.S. PATENT DOCUMENTS

| | | | |
|---|---|---|---|
| 3,697,451 | 10/1972 | Mausner | 252/174.12 X |
| 3,817,838 | 6/1974 | Harris | 435/19 |
| 3,853,465 | 12/1974 | Rush | 23/230 B |
| 3,855,142 | 12/1974 | Pader | 252/174.12 X |
| 3,950,277 | 4/1976 | Stewart | 252/174.12 X |
| 4,011,045 | 3/1977 | Bonderman | 252/408 |
| 4,184,848 | 1/1980 | Batz | 23/230 B |
| 4,226,713 | 10/1980 | Goldberg | 23/230 B |
| 4,259,440 | 3/1981 | Gupta | 435/19 |
| 4,268,171 | 5/1981 | Sternberg | 23/230 B |
| 4,273,867 | 6/1981 | Lin | 23/230 B |

*Primary Examiner*—Sidney Marantz
*Attorney, Agent, or Firm*—Curtis, Morris & Safford

[57] ABSTRACT

The invention relates to a process for the quantitative determination of a serum protein, especially apolipoprotein, in turbid serum or plasma samples by nephelometry, which comprises, after having carried out an immunologic reaction with the corresponding antibody, measuring in the presence of a tenside of the formula $$CH_3-(CH_2)_m-R-(CH_2-CH_2-O)_n-H \qquad (I)$$

in which

R is $-O-$; $-NH-$; $-CH=CH-(CH_2)_x-NH$;

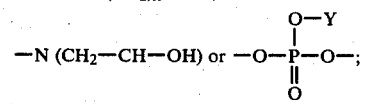

$$-N(CH_2-CH-OH) \text{ or } -O-\overset{\overset{\displaystyle O-Y}{|}}{\underset{\underset{\displaystyle O}{\|}}{P}}-O-;$$

Y is $H-$ or $CH_3-(CH_2)_q-$, m and q, being identical or different; each are an integer of from 6 to 26, preferably 6 to 18; n is an integer of from 7 to 50, preferably 7 to 25; and x is 7 or 8; the tenside being used in a concentration of from $10^{-3}$ to $10^{-1}\%$ by volume. Alternatively, the measures can be taken after enzymatic degradation of the lipids and subsequent immunologic reaction with the corresponding antibody in the presence of a nonionic tenside of the formula (I), in which R is as defined above, or

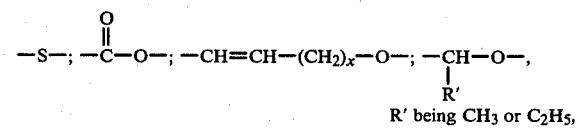

$$-S-; -\overset{\overset{\displaystyle O}{\|}}{C}-O-; -CH=CH-(CH_2)_x-O-; -\underset{\underset{\displaystyle R'}{|}}{CH}-O-,$$

R' being $CH_3$ or $C_2H_5$,

Further subjects of the invention are the use of a tenside of the cited formula for serum work-up for quantitative determination of an apolipoprotein, and an agent for serum work-up for quantitative determination of an apolipoprotein, consisting of a mixture of at least one lipid-degrading enzyme and a tenside of the cited formula.

4 Claims, 6 Drawing Figures

PROCESS FOR THE QUANTITATIVE DETERMINATION OF A SERUM PROTEIN IN TURBID SERUM AND PLASMA SAMPLES

The invention relates to a process for the quantitative determination of a serum protein, especially of an apolipoprotein, in turbid serum and plasma samples, by nephelometry.

For determining serum proteins, especially apolipoproteins, there are known automatic nephelometry processes which, however, are suitable only for normolipemic sera, while in the case of hyperlipemic, especially hypertriglyceridemic, sera the values obtained in the processes prove to be excessive.

Recently, methods applying laser nephelometry have been developed for quantitative determination of immunoglobulins and other serum proteins, where addition of polyethyleneglycol (PEG) has proved to be advantageous. In the presence of PEG, a characteristic enhancement phenomenon has been observed which is due to increased turbidity.

Quantitative determination of serum proteins, especially protein portions, in serum lipoproteins by nephelometry is handicapped by the autoturbidity of hyperlipemic sera, that is, sera containing large amounts of triglycerides and/or cholesterol. In these cases, nephelometry of an immunologic reaction in non-pretreated serum samples gives results which often exceed considerably those of usual comparable processes. Even when taking into consideration the auto-turbidity of a serum in the determination of apolipoproteins, there cannot be obtained substantially better results, because the size of immunocomplexes of monospecific antibodies and an apolipoprotein in intact lipoproteins, apart from the apolipoprotein portion, depends on the content of especially triglyceride and cholesterol esters in the lipoprotein, too, and thus may cause different turbidity behavior. Determination of apolipoproteins by quantitative nephelometry of immunoprecipitates in the presence of PEG has likewise proved to be impracticable, because in this case, a pronounced unspecific turbidity develops.

There are known two ways for reducing the turbidity produced by lipids:
(1) by adding tensides clarifying the turbidity, and
(2) by hydrolytic degradation of lipids in intact lipoproteins.

Clarification of serum samples by adding nonionic tensides has been described (Bergmeyer, H. U., Enzymatische Analyse, 2nd ed. (1970), vol. 1, pp. 547–549 and 759–763). Especially, fatty acids esters or fatty alcohol ethers have proved to be suitable for this operation, where the tensides are used in a concentration of from 0.2 to 20% by volume. Although at this concentration enzymatic activity or metabolites of the human body can be quantitatively evaluated in serum samples, according to further test results immunologic reactions of an antibody and an apolipoprotein in an intact serum lipoprotein are inhibited by a concentration of 0.1% by volume or more of these tensides. Accordingly, there is insufficient conformity of an immunologic determination of apolipoproteins in a turbid serum by nephelometry under conditions which are sufficient for measuring enzymes or metabolites with one of the usual processes (for example radial immunodiffusion).

The auto-turbidity of a lipemic serum can alternatively be reduced by enzymatic degradation of lipids in intact lipoproteins. In the case of hydrolysis of lipids the extent of turbidity development, for example in the immunologic reaction of apolipoproteins in Very Low Density Lipoproteins (VLDL) and the corresponding antibody, is reduced as compared to a non-pretreated serum. However, the results of the quantitative determination of apolipoproteins by means of laser nephelometry after such an enzymatic pretreatment of lipemic sera are insufficient as compared to those obtained according to the methods of radial immunodiffusion or immuno-electrophoresis according to Laurell.

Surprisingly, it has been found that satisfactory results are obtained by measuring in the presence of a tenside of the formula $$CH_3-(CH_2)_m-R-(CH_2-CH_2-O)_n-H \qquad (I)$$

in which

R is $-O-$; $-NH-$; $-CH=CH-(CH_2)_x-NH$;

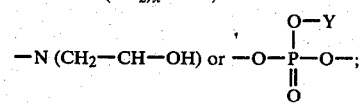

$-N(CH_2-CH-OH)$ or $-O-\overset{O-Y}{\underset{\underset{O}{\|}}{P}}-O-$;

Y is $H-$ or $CH_3-(CH_2)_q-$ m and q, being identical or different, each are an integer of from 6 to 26, preferably 6 to 18;
n is an integer of from 7 to 50, preferably 7 to 25; and
x is 7 or 8;
the tenside being used in a concentration of from $10^{-3}$ to $10^{-1}$% by volume.

In accordance with the invention, an alternative process variant comprises, after enzymatic degradation of the lipids and subsequent immunologic reaction with the corresponding antibody, measuring in the presence of a non-ionic tenside of the formula (I), in which R is as defined above or

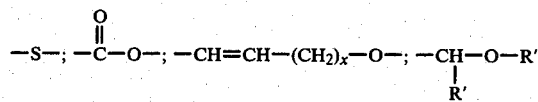

being $CH_3$ or $C_2H_5$, and X is as defined above; the tenside being used in a concentration of from $10^{-3}$ to $10^{-1}$% by volume.

Preferably, measuring is carried out by means of nephelometry, which allows a quantitative determination of, for example, apolipoproteins in human serum in a faster, simpler and less expensive manner than hitherto obtained by usual methods.

The invention relates furthermore to the use of a tenside of the formula $CH_3-(CH_2)_m-R-(CH_2-CH_2-O)_n-H$, in which R, m and n are as defined above, in a concentration of from $10^{-3}$ to $10^{-1}$% by volume, for serum work-up for quantitative determination of an apolipoprotein.

The invention relates furthermore to an agent for serum work-up for quantitative determination of an apolipoprotein, which consists of a mixture of a tenside of the formula (I), in which R, R', m and n and x are as defined above, and at least one lipid-degrading enzyme.

Figure 2:
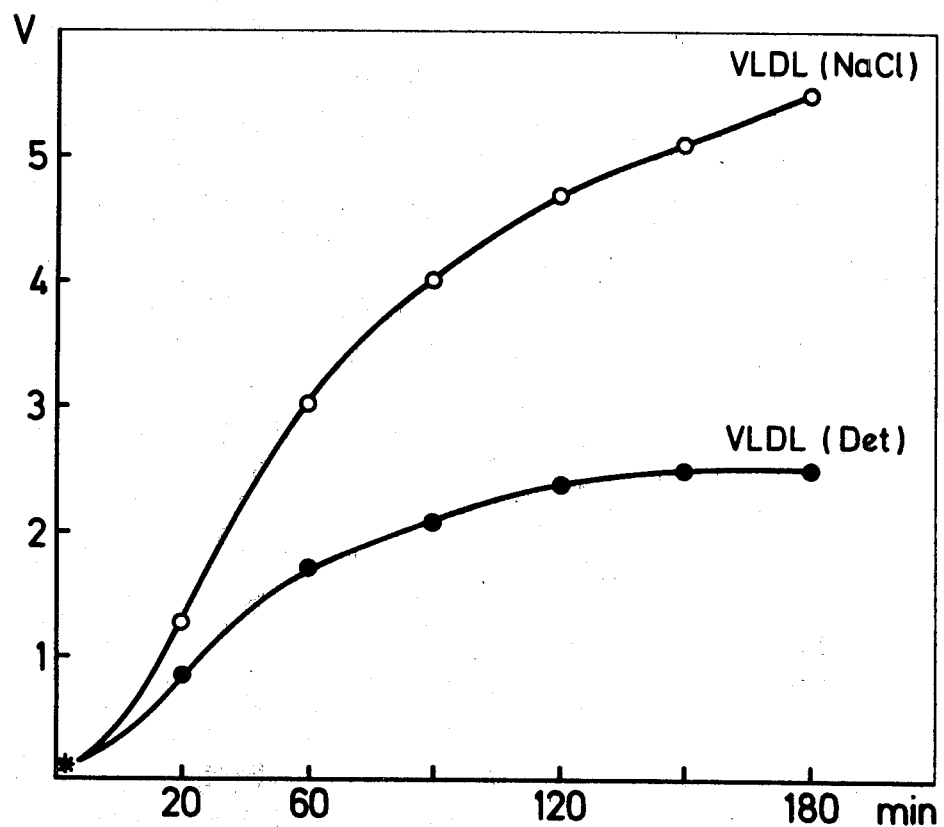
Figure 2:
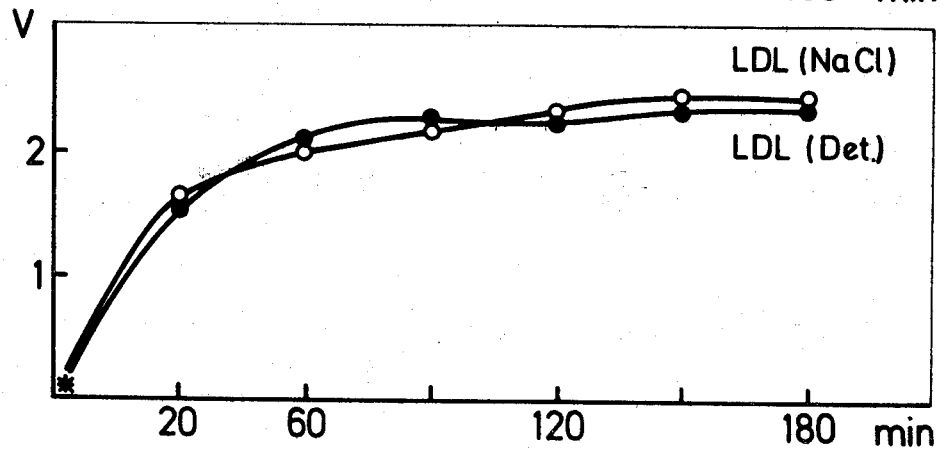
Figure 3:
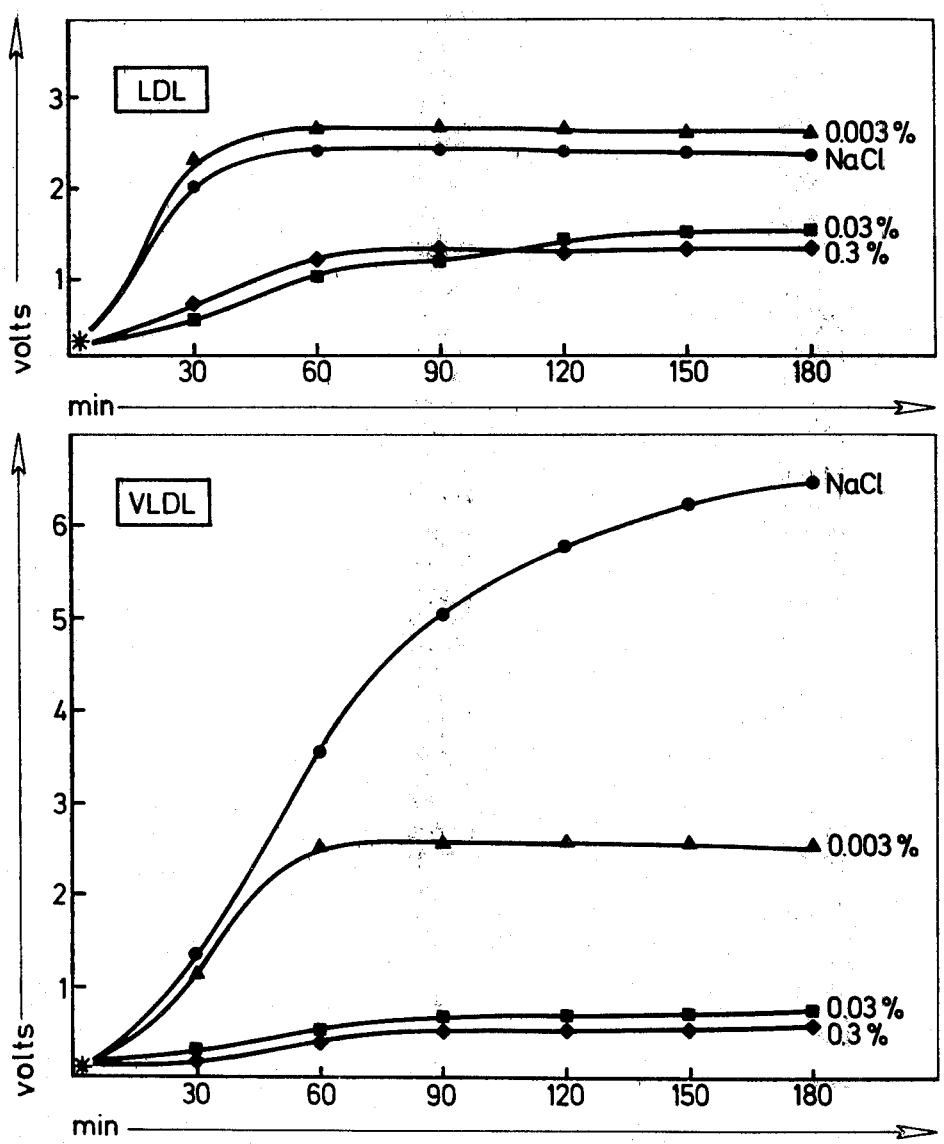
Figure 4:
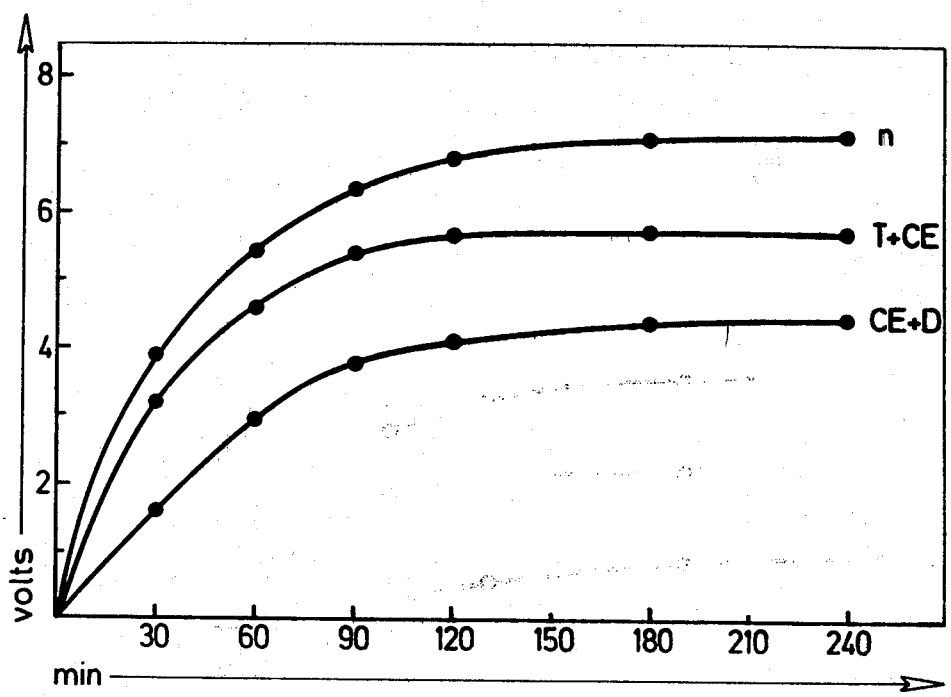
Figure 5:
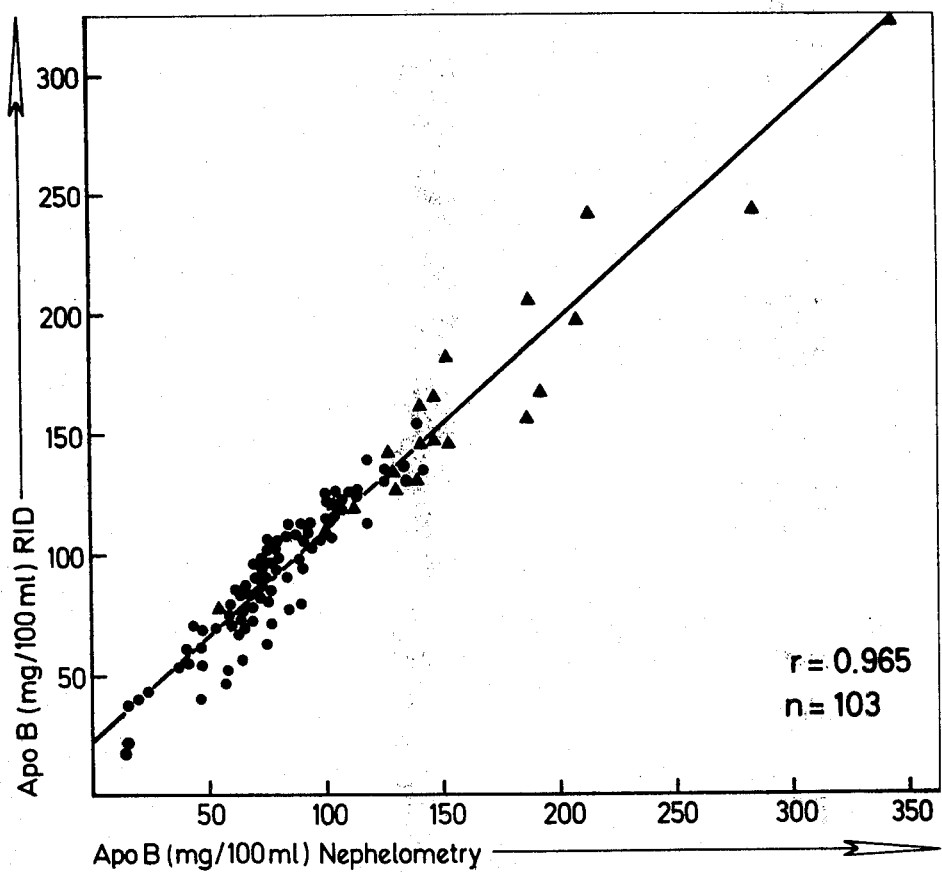
Figure 6:
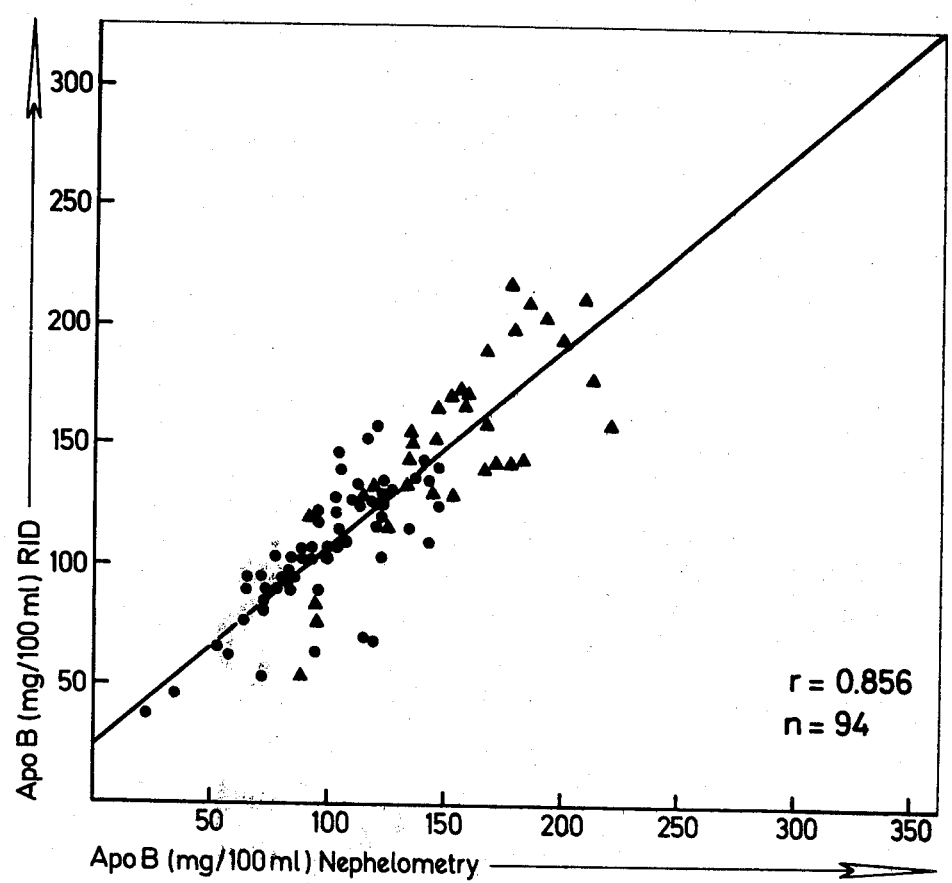

The invention will better understood by reference to the accompanying drawings, which show
in FIG. 1: the development of turbidity by immunoprecipitates from the reaction of anti-apolipoprotein B in isolated LDL and isolated VLDL;

in FIG. 2: the clarification effect of the antigen/antibody reaction in isolated VLDL or LDL by addition of a tenside;

in FIG. 3: the influence of the emulsifier concentration on the turbidity development of an immunologic reaction of anti-apolipoprotein B and apo-lipoprotein B in intact VLDL or LDL;

in FIG. 4: the turbidity development of the immunologic reaction of anti-apolipoprotein B and apolipoprotein B in the serum after pretreatment with different enzymes;

in FIG. 5: a comparison of the process of the invention with that of radial immunodiffusion on normotriglyceridemic sera;

in FIG. 6: a comparison of the two processes cited on hyper-triglyceridemic sera.

Laboratory diagnosis of lipometabolic disturbances is carried out according to the recommendations of Frederickson. Usually, the concentration of cholesterol and triglycerides is measured in the serum or plasma, and in serum lipoproteins fractionated according to different methods. However, these tests allow to obtain symptomatic evidence only on the kind of lipometabolic disturbance in question. From recent research results, however, it is known that apolipoproteins, being components of the lipoproteins of the serum, have an important function in the biochemistry of the lipometabolism, where some of them act as activators, and some as inhibitors of lipolytic enzymes. The physiological function of some apolipoproteins is not yet fully explained.

Among the nine apolipoproteins hitherto known, that is, Apo—$A_1$, —$A_2$, —B, —$C_1$, —$C_2$, —$C_3$, —D, —E, —F, the apolipoprotein B is distinguished by forming the substantial protein component (84–94%) of the Low Density Lipoproteins (LDL), wherein the largest amount of serum cholesterol is conveyed. In the Very Low Density Lipoproteins (VLDL), 40 to 50% of the protein portion consist of apolipoprotein B. Being an integral part of these lipoprotein classes, it is a protein complement for cellular receptors which control the feed of cholesterol to the cell, and thus influence directly the intracellular synthesis of cholesterol. Therefore, it is especially important in view to the development of arteriosclerosis.

For these reasons, the following description relates mainly to the determination of apolipoprotein B, without, however, excluding application of the process of the invention for determing the remaining apolipoproteins or further serum proteins.

The following Table shows the correlation of the determination of an apolipoprotein in samples of human serum by means of laser nephelometry and of radial immunodiffusion. The volume concentration of the tenside was a final $3 \times 10^{-3}\%$. In the case of c, it was $3 \times 10^{-2}\%$, and in the case of d $6 \times 10^{-3}$. In the latter test series, a cationic tenside was used, in which R stands for $-CH=CH-(CH_2)_7-NH$.

In further test series, a nonionic tenside was used wherein

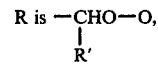

$R'$ is $C_2H_5$, m is 9 and n is 10.

In the Table, N represents the number of serum samples examined,

|  | test batch | N | Tg | Chol | a | b | r |
|---|---|---|---|---|---|---|---|
| (a) + | 0.9% NaCl | 176 | 47–4300 | 47–930 | 0.515 | +51.63 | 0.727 |
| (b) + | nonionic tenside ($3 \times 10^{-3}\%$) | 176 | 47–4300 | 47–930 | 0.577 | +49.72 | 0.758 |
| (c) + | nonionic tenside ($3 \times 10^{-2}\%$) | | standardization impossible | | | | |
| (d) + | cationic tenside ($6 \times 10^{-3}\%$) | 203 | 60–2950 | 96–954 | 0.770 | +22.06 | 0.890 |
| (e) + | triglyceride lipase (3 U) | 54 | 52–1535 | 133–725 | 0.250 | +83.42 | 0.559 |
| (f) + | cholesterol esterase (200 mU) | 54 | 52–1535 | 133–725 | 0.491 | +63.86 | 0.613 |
| (g) + | triglyceride lipase + cholesterol esterase | 72 | 49–1200 | 96–800 | 0.804 | +26.57 | 0.820 |
| (h) + | phospholipase D + cholesterol esterase | 127 | 47–2700 | 42–1400 | 0.374 | +59.42 | 0.727 |
| (i) + | triglyceride lipase + cholesterol esterase + nonionic tenside ($3 \times 10^{-3}\%$) | 198 | 47–2700 | 42–1400 | 0.846 | +23.71 | 0.9262 |
| (j) + | phospholipase D + cholesterol esterase + nonionic tenside ($3 \times 10^{-3}\%$) | 199 | 47–2700 | 42–1400 | 0.629 | +39.59 | 0.883 |
| (k) | neuraminidas (60 mU) cholesterol esterase (200 mU) nonionic tenside ($3 \times 10^{-3}\%$) | 89 | 52–1790 | 100–450 | 1.423 | −3.76 | 0.905 |
| (l) | neuraminidase (60 mU) + triglyceride lipase (3 U) + nonionic tenside ($3 \times 10^{-3}\%$) | 60 | 56–550 | 151–601 | 0.816 | +32.82 | 0.801 |

Tg represents the triglyceride concentration (limit value in mg/dl)
Chol represents the cholesterol concentration (limit value in mg/dl)
a represents the slope of the regression line $y_{RID} = a \cdot x_{neph} + b$
b represents the intersection of the regression line and y axis
r represents the correlation.

It results from the Table that tensides of the above formula (I) in the final concentration as indicated give a satisfactory correlation.

When using nonionic tensides, an additional enzymatic degradation of the lipids is useful. However, a too high concentration of tenside renders standardization impossible.

The following enzymes have proved to be suitable for enzymatic degradation of lipids or neuraminicsiolic acid:

| | | |
|---|---|---|
| Triglyceride lipase | (EC. 3.1.1.3) | 0.5–10 U |
| Cholesterol esterase | (EC. 3.1.1.13) | 20–500 mU |
| Phospholipase D | (EC. 3.1.4.4) | 10–100 mU |
| Neuraminidase | (EC. 3.2.1.18) | 10–150 mU |
| Phospholipase C | (EC. 3.1.4.3) | 5–500 mU |
| Carboxylic esterase | (EC. 3.1.1.1) | 0.1–100 U |

A combination of different enzymes (for example triglyceride lipase and cholesterol esterase) has proved to give better results than the use of one single enzyme (for example triglyceride lipase or cholesterol esterase).

Nephelometry consists in measuring the intensity of scattered light. Apart from the technical parameters of apparatus, the intensity of scattered light depends on the number of particles, for example of immunocomplexes, present in a solution. The intensity of scattered light is furthermore influenced by the volume of the particles. Lipoproteins, being among the largest non-cellular spheric components of a serum, at a size of from $10^4$ to $10^6$ Å, cause auto-turbidity of the serum even without forming a complex with an antibody.

Because of the different size of the individual kinds of lipoproteins it was to be expected that the turbidity caused by immunoprecipitates from the reaction of anti-apolipoprotein B with apolipoprotein B in LDL and VLDL isolated from each other would develop in a differing manner, which expectation was fully confirmed by corresponding tests (see FIG. 1).

The content of apolipoprotein B measured by immunoelectrophoresis according to Laurell was 82 mg/dl in LDL, and 40 mg/dl in VLDL. The comparison of turbidity development at 23° C. in both lipoprotein classes shows that the immunoreaction on VLDL proceeds more slowly until reaching the turbidity maximum than the same reaction on LDL. Moreover, the turbidity in VLDL develops more intensely than in LDL, despite the lower content of apolipoprotein B.

Furthermore, the influence of the tensides on the antigen/antibody reaction has been examined (FIG. 2).

The individual lipoprotein fractions (Very Low Density Lipoproteins, VLDL, and Low Density Lipoproteins, LDL) were isolated according to known methods by means of ultracentrifugation. The samples were diluted at 23° C. in a ratio of 1+100, either with a 0.9% NaCl solution or with a $10^{-2}$% tenside solution (m=12 and n=9).

Dilution was carried out at temperatures of from 15° to 54° C. Subsequently, 1 part of the corresponding dilute sample was mixed with 2 parts of an apo-B-antibody solution (diluted with a physiological saline solution at a ratio of 1+5). The development of turbidity was measured at 23° C. for a period of 180 minutes by means of a laser nephelometer.

The comparison of the test on VLDL and LDL (FIG. 2) demonstrates that the extent of developing turbidity in the presence of the tenside (as compared to an identical test where the sample was diluted with a physiological saline solution) is decreased in the VLDL fraction only, while in the same reaction an insignificant influence of the tenside on LDL is stated. In the presence of the tenside, the turbidity maximum in the reaction on VLDL is attained earlier than in the corresponding test using physiological saline solution.

In further tests, lipoproteins were diluted in a ratio of 1+100 with a saline solution or a tenside solution having a different final concentration by volume ($3\times10^{-1}$%, $3\times10^{-2}$%, $3\times10^{-3}$%) (FIG. 3). The antibody solution was mixed with the dilute samples in the same ratio as indicated above. A comparison of the turbidity development in the antigen/antibody reaction confirmed the observation that the tenside of the m=9, R'=$C_2H_5$, n=10 type used inhibits the immunoreaction at elevated concentration (0.3% by volume).

FIG. 4 shows the examination of a hyperlipemic serum (triglyceride content: 840 mg/dl, cholesterol content: 33 mg/dl). The serum was diluted with physiological saline solution in a ratio of 1×100. An aliquot of 300 μul was preliminarily incubated for 30 minutes at 23° C. with 20 μul of an enzyme solution of either 3 units of triglyceride lipase and 200 milliunits of cholesterol esterase (T+CE), or of 50 milliunits of phospholipase D and 200 milliunits of cholesterol esterase (CE+D). (Alternatively, the enzymes may be added in dissolved state in the tenside solution.) Subsequently, an antibody solution was added in the above ratio, and the developing turbidity was observed for a period of 4 hours.

Comparison of the turbidity development after a pretreatment with different lipases confirms the decrease of turbidity development. This reduction can be assumed to be due to the effect of the lipase, namely hydrolytic degradation of lipids in the lipoproteins. The kinetic course moreover proves that after pretreatment with the lipases the maximum of turbidity development is attained earilier than in the case of a non-pretreated serum sample.

The turbidity development can be measured quantitatively by nephelometry.

Comparative tests on sera having a hyperlipemia the content of apolipoprotein B of which was determined according to the process as described below show a high degree of conformity with the values obtained according to other determination processes (radial immunodiffusion, immuno-electrophoresis according to Laurell).

The serum samples were diluted in a 1+100 ratio with a physiological saline solution or a 0.01% tenside solution of the m=9, n=10 and R'=$C_2H_5$ type, and preliminarily incubated for 30 minutes with the enzyme combinations. Subsequently, the pretreated samples were worked up as described above with an anti-apolipoprotein B serum. All reactions were carried out at 23° C. The final value of turbidity was read 2 hours after addition of the antibody.

The comparison of the test results demonstrates that neither the addition of anonionic tenside alone nor the sole preliminary incubation of the serum samples with lipolytic enzymes gives measuring results which correspond to the data obtained by radial immunodiffusion in a degree satisfactory for laboratory diagnosis. In contrast thereto, a combined process, where a tenside is added as well as a preliminary incubation with lipolytic enzymes for degrading the lipids present in lipoproteins is carried out, gives more than 90% of conformity of the measuring results with those of radial immunodiffusion over the complete range of triglyceride concentration up to 2700 mg/dl and of cholesterol concentration up to 1400 mg/dl which may occur in a serum.

A differentiated comparison of determination of apolipoprotein B from sera of persons having a normoor hypertriglyceridemia was carried out by means of radial immunodiffusion and of laser nephelometry.

FIG. 5 shows a comparison of the two processes on normotriglyceridemic sera (normolipemia and hyperlipoproteinemia of type IIa).

Sera having a cholesterol concentration of less than 280 mg/dl: ○

Sera having a cholesterol concentration of more than 280 mg/dl: ▲)

The following correlation line results: $y_{RID} = 0.875 \, X_{neph} + 22.5$

FIG. 6 shows a comparison of the two processes on hypertriglyceridemic sera (hyperlipoproteinemia of types IV, V and IIb).

Sera having a cholesterol concentration of less than 280 mg/dl: ○

Sera having a cholesterol concentration of more than 280 mg/dl: ▲)

In this case, the following correlation line results: $y_{RID} = 0.823 \, X_{neph} + 24.7$

What is claimed is:

1. A process for the quantitative determination of a serum protein in a turbid serum or plasma sample by nephelometry which comprises the steps of immunologically reacting said serum protein with an antibody therefor and measuring the intensity of scattered light therefrom in the presence of from $10^{-3}$ to $10^{-1}\%$ by volume of a tenside of the formula $$CH_3-(CH_2)_m-R-(CH_2-CH_2-O)_n-H$$

in which

R is $-O-$; $-NH-$; $-CH=CH-(CH_2)_x-NH$, 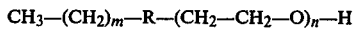

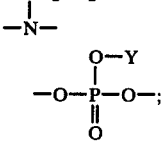

Y is H or $(CH_2)_q CH_3$;

m and q, which may be identical or different, stand for integers of from 6 to 26, preferably 6 to 18;

n is an integer of from 7 to 50, preferably 7 to 25; and x is 7 or 8.

2. Process as defined in claim 1 wherein the serum protein is apolipoprotein.

3. A process for the quantitative determination of an apolipoprotein in a turbid serum or plasma sample by nephelometry which comprises, after enzymatic degradation of the lipids and subsequent immunologic reaction thereof with the antibody therefor, measuring the intensity of scattered light therefrom in the presence of from $10^{-3}$ to $10^{-1}\%$ by volume of a nonionic tenside of the formula $$CH_3-(CH_2)_m-R-(CH_2CH_2O)_n H$$

in which

R is $-O-$, $-S-$, $-NH-$, $-\underset{\underset{O}{\|}}{C}O-$, $-CH=CH(CH_2)_x-NH-$, $-CH=CH-(CH_2)_x-O-$, $-\underset{\underset{CH_2CH_2OH}{|}}{N}-$, $-O-\underset{\underset{O}{\|}}{P}-O-$ or $-\underset{\underset{R^1}{|}}{C}HO-$;

Y is H or $(CH_2)_q CH_3$; R' is $CH_3$ or $C_2H_5$;

m and q, which may be identical or different, stand for integers of from 6 to 26, preferably 6 to 18;

n is an integer from 7 to 50, preferably 7 to 25; and x is 7 or 8.

4. Agent for serum work-up for quantitative determination of an apolipoprotein, which consists of a mixture of at least one lipid-degrading enzyme and a tenside as defined in claim 3.

* * * * *